United States Patent

Reiffenrath et al.

[11] Patent Number: 5,232,624
[45] Date of Patent: Aug. 3, 1993

[54] CHIRAL 1,2-DIFLUOROBENZENE DERIVATIVES

[75] Inventors: Volker Reiffenrath, Rossdorf; Joachim Krause, Dieburg; Andreas Wächtler, Griesheim; Thomas Geelhaar, Mainz; Ekkehard Bartmann, Erzhausen; Reinhard Hittich, Modautal, all of Fed. Rep. of Germany

[73] Assignee: Merck Patent Gesellschaft Mit Beschrankter Haftung, Darmstadt, Fed. Rep. of Germany

[21] Appl. No.: 359,663
[22] PCT Filed: Feb. 28, 1989
[86] PCT No.: PCT/EP89/00191
§ 371 Date: May 15, 1989
§ 102(e) Date: May 15, 1989
[87] PCT Pub. No.: WO89/08639
PCT Pub. Date: Sep. 21, 1989

[30] Foreign Application Priority Data

Mar. 10, 1988 [DE] Fed. Rep. of Germany ....... 3807802

[51] Int. Cl.$^5$ .................. C09K 19/34; C09K 19/12; C07D 239/02; C07D 211/70
[52] U.S. Cl. .................. 252/299.61; 252/299.66; 544/298; 546/339
[58] Field of Search ............... 544/298, 360; 546/339; 252/299.61, 299.66; 568/631, 633, 647, 639

[56] References Cited

U.S. PATENT DOCUMENTS

| 4,368,135 | 1/1983 | Osman | 252/299.63 |
| 4,415,470 | 11/1983 | Eidenschink et al. | 252/299.63 |
| 4,514,317 | 4/1985 | Tuong et al. | 252/299.63 |
| 4,545,922 | 10/1985 | Eidenschink et al. | 252/299.63 |
| 4,551,264 | 11/1985 | Eidenschink et al. | 252/299.63 |
| 4,602,851 | 7/1986 | Jenner et al. | 359/103 X |
| 4,606,845 | 8/1986 | Romer et al. | 252/299.63 |
| 4,637,897 | 1/1987 | Kelly | 252/299.63 |
| 4,659,502 | 4/1987 | Fearon et al. | 252/299.61 |
| 4,664,840 | 5/1987 | Osman | 252/299.63 |
| 4,710,315 | 12/1987 | Schad et al. | 252/299.63 |
| 4,724,097 | 2/1988 | Romer et al. | 252/299.63 |
| 4,776,973 | 10/1988 | Bofinger et al. | 252/299.61 |
| 4,820,839 | 4/1989 | Krause et al. | 544/316 |
| 4,834,904 | 5/1989 | Krause et al. | 252/299.01 |
| 4,874,544 | 10/1989 | Yong et al. | 252/299.61 |
| 4,886,619 | 12/1989 | Janulis | 252/299.1 |
| 4,897,216 | 1/1990 | Reiffenrath et al. | 252/299.63 |
| 4,925,278 | 5/1990 | Buchecker et al. | 359/103 X |
| 4,925,590 | 5/1990 | Reiffenrath et al. | 252/299.61 |
| 4,943,384 | 7/1990 | Sucrow et al. | 252/299.61 |
| 5,087,764 | 2/1992 | Reiffenrath et al. | 568/656 |
| 5,089,168 | 2/1992 | Krause et al. | 252/299.61 |

FOREIGN PATENT DOCUMENTS

| 0051738 | 3/1981 | European Pat. Off. |
| 0133489 | 7/1984 | European Pat. Off. |
| 1229842 | 10/1986 | Japan .................. 560/65 |
| WO88/02130 | 3/1988 | World Int. Prop. O. |

Primary Examiner—Robert L. Stoll
Assistant Examiner—C. Harris
Attorney, Agent, or Firm—Millen, White, Zelano & Branigan

[57] ABSTRACT

Chiral 1,2-difluorobenzene derivatives are suitable as components of chiral tilted smectic liquid-crystalline phases.

4 Claims, No Drawings

CHIRAL 1,2-DIFLUOROBENZENE DERIVATIVES

The invention relates to chiral 1,2-difluorobenzene derivatives of the formula I

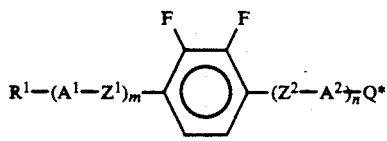

in which

R$^1$ is H, F, Cl, Br, CN, an alkyl or perfluoroalkyl group each having 1 to 12 C atoms and in which, in addition, one or two non-adjacent CH$_2$ or CF$_2$ groups may be replaced by O atoms and/or —CO— groups and/or —CO—O— groups and/or —CH=CH— groups and/or —CHhalogen— and/or —CHCN— groups and/or —O—CO—halogen and/or —CO—O—CHCN— groups, A$^1$ and A$^2$, in each case independently of one another, are 1,4-phenylene which is unsubstituted or substituted by one or two F and/or Cl atoms and/or CH$_3$ groups and/or CN groups and in which, in addition, one or two CH groups may be replaced by N, or are 1,4-cyclohexylene in which, in addition, one or two non-adjacent CH$_2$ groups may be replaced by O atoms and/or S atoms, or are piperidine-1,4-diyl, 1,4-bicyclo(2,2,2)octylene, 1,3,4-thiadiazole-2,5-diyl, naphthalene-2,6-diyl, decahydronaphthalene-2,6-diyl or 1,2,3,4-tetrahydronaphthalene-2,6-diyl, Z$^1$ and Z$^2$ are each —CO—O, —O—CO—, —CH$_2$CH$_2$—, —OCH$_2$—, —CH$_2$O—, —C≡C— or a single bond, m is 0, 1 or 2, n is 1 or 2, (m+n) is 1 or 2, and Q* is a chirally-inducing organic radical having an asymmetric carbon atom.

Like similar compounds described in German Offenlegungsschrift 3,515,373, the compounds of the formula I can be used as components of chiral tilted smectic liquid-crystalline phases.

Chiral tilted smectic liquid-crystalline phases having ferroelectric properties can be prepared by adding a suitable chiral dope to base mixtures having one or more tilted smectic phases (L. A. Beresnev et al., Mol. Cryst. Liq. Cryst. 89, 327 (1982); H. R. Brand et al., J. Physique 44, (lett.), L-771 (1983). Phases of this type can be used as dielectrics for rapidly switching displays based on the principle of SSFLC technology described by Clark and Lagerwall (N. A. Clark and S. T. Lagerwall, Appl. Phys. Lett. 36, 899 (1980); U.S. Pat. No. 4,367,924) on the basis of the ferroelectric properties of the chiral tilted phase. In this phase, the long molecules are arranged in layers, the molecules having a tilt angle to the layer perpendiculars. On moving from layer to layer, the tilt direction changes by a small angle with respect to an axis perpendicular to the layers, thus forming a helical structure. In displays based on the principle of SSFLC technology, the smectic layers are arranged perpendicular to the plates of the cell. The helical arrangement of the tilt directions of the molecules is suppressed by a very small separation of the plates (about 1-2 μm). The longitudinal axes of the molecules are therefore forced to arrange themselves in a plane parallel to the plates of the cell, thus causing two preferred tilt orientations. By applying a suitable electrical alternating field, it is possible to switch back and forth between these two states in the liquid crystalline phase exhibiting spontaneous polarization. This switching process is considerably faster than in customary twisted cells (TN-LCDs) based on nematic liquid crystals.

It is a great disadvantage for many applications of the currently available materials having chiral tilted smectic phases (such as, for example, Sc*) that they have a relatively high optical anisotropy and unacceptably short switching times, due to relatively high viscosity values, and that the dielectric anisotropy values are greater than zero or, if they are negative, have values only slightly different from zero. Negative values for the dielectric anisotropy are necessary if the planar orientation necessary is caused by overlapping the control field with an AC holding field of small amplitude (J. M. Geary, SID Congress, Orlando/Fla., April/May 1985, Paper 8.3).

It has now been found that the use of compounds of the formula I as components of chiral tilted smectic mixtures can significantly reduce the disadvantages mentioned. The compounds of the formula I are thus pre-eminently suitable as components of chiral tilted smectic liquid-crystalline phases. In particular, they can be used to prepare chiral tilted smectic liquid-crystalline phases which are particularly stable chemically and have favourable ferroelectric phase ranges, in particular broad Sc* phase ranges, negative or positive dielectric anisotropy, low optical anisotropy, a favourable pitch level, low viscosity and values for spontaneous polarization which are high for phases of this type, and very short switching times. P is the spontaneous polarization in nC/cm$^2$.

In addition, the provision of the compounds of the formula I very generally considerably broadens the range of liquid-crystalline substances which are suitable, from various applicational points of view, for the preparation of ferroelectric mixtures.

The compounds of the formula I have a broad range of application. Depending on the choice of substituents, these compounds can be used as base materials of which liquid-crystalline phases are predominantly composed; however, it is also possible to add compounds of the formula I to liquid-crystalline base materials from other classes of compound, in order, for example, to vary the dielectric and/or optical anisotropy and/or the spontaneous polarization and/or the phase range and/or the tilt angle and/or the pitch and/or the switching times of a phase of this type. The compounds of the formula I are furthermore suitable as intermediates in the preparation of other substances which can be used as components of liquid-crystalline phases.

In the pure state, the compounds of the formula I are colourless and have low optical anisotropy values. Some of the compounds of the formula I exhibit liquid-crystal-line mesophases in a temperature range which is in a favourable position for electrooptical use, but isotropic or monotropically liquid-crystalline compounds of the formula I can also be employed advantageously as components of chiral tilted smectic phases. They are very stable chemically, thermally and to light.

The invention thus relates to the compounds of the formula I, and to the use of the compounds of the formula I as components of liquid-crystalline phases.

The invention also relates to chiral tilted smectic liquid-crystalline phases containing at least one compound of the formula I and at least one carbon atom linked to four different substituents.

The invention furthermore relates to phases of this type containing at least one compound of the formula I and to liquid-crystal display elements, in particular ferroelectric electrooptical display elements, which contain phases of this type.

For reasons of simplicity, Ph below is a 1,4-phenylene group which is unsubstituted or substituted by one or two fluorine atoms and in which, in addition, one or two CH groups may be replaced by N, Cy is a 1,4-cyclohexylene group in which, in addition, one or two non-adjacent $CH_2$ groups may be replaced by O atoms, Thi is a 1,3,4-thiadiazole-2,5-diyl group, and Bi is a bicyclo(2,2,2)octylene group. $PheF_2$ is a group of the formula

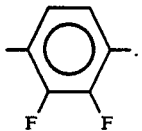

Above and below, $Q^*$, $A^1$, $A^2$, $Z^1$, $Z^2$, m and n have the meaning indicated, unless expressly stated otherwise.

Accordingly, the compounds of the formula I include, in particular, compounding indicated, rmulae Ia to Id (having two rings)

$R^1$-$PheF_2$-$A^2$-$Q^*$      Ia $R^1$-$PheF_2$-$Z^2$-$A^2$-$Q^*$      Ib $Q^*$-$PheF_2$-$A^2$-$R^1$      Ic $Q^*$-$PheF_2$-$Z^2$-$A^2$-$R^1$      Id and Ie to It (having three rings):

$R^1$-$PheF_2$-$A^2$-$A^2$-$Q^*$      Ie $R^1$-$PheF_2$-$Z^2$-$A^2$-$A^2$-$Q^*$      If $R^1$-$PheF_2$-$A^2$-$Z^2$-$A^2$-$Q^*$      Ig $R^1$-$PheF_2$-$Z^2$-$A^2$-$Z^2$-$A^2$-$Q^*$      Ih $R^1$-$A^1$-$PheF_2$$A^2$-$Q^*$      Ii $R^1$-$A^1$-$Z^1$-$PheF_2$-$A^2$-$Q^*$      Ij $R^1$-$A^1$-$PheF_2$-$Z^2$-$A^2$-$Q^*$      Ik $R^1$-$A^1$-$Z^1$-$PheF_2$-$Z^2$-$A^2$-$Q^*$      Il $Q^*$-$PheF_2$-$A^2$-$A^2$-$R^1$      Im $Q^*$-$PheF_2$-$Z^2$-$A^2$-$A^2$-$R^1$      In $Q^*$-$PheF_2$-$A^2$-$Z^2$-$A^2$-$R^1$      Io $Q^*$-$PheF_2$-$Z^2$-$A^2$-$Z^2$-$A^2$-$R^1$      Ip $Q^*$-$A^1$-$PheF_2$-$A^2$-$R^1$      Iq $Q^*$-$A^1$-$Z^1$-$PheF_2$-$A^2$-$R^1$      Ir $Q^*$-$A^1$-$PheF_2$-$Z^2$-$A^2$-$R^1$      Is $Q^*$-$A^1$-$Z^1$-$PheF_2$-$Z^2$-$A^2$-$R^1$      It

Of these, those of the formulae Ia, Ic, Ie, Im, In and If are particularly preferred. Particularly preferred compounds are those of the formula I'

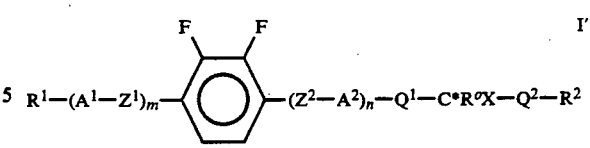

in which $Q^1$, $Q^2$, $R^o$ and X are as defined in claim 2. $R^b$ is an alkyl group which is different from X and $Q^2$—$R^2$ and preferably has 1 to 5 C atoms. Methyl and ethyl, in particular methyl, are particularly preferred. $R^2$ is preferably an alkyl group having 2 to 10, in particular 2 to 6, C atoms. $Q^1$ and $Q^2$ are preferably, in each case independently of one another, —O—CO— (where the carbonyl carbon atom is linked to the asymmetric C atom $C^*$), —O—$CH_2$— (where the methylene group is linked to the asymmetric C atom $C^*$), —$CH_2CH_2$—, —$CH_2$— or a single bond (—). Particularly preferred combinations of $Q^1$ and $Q^2$ are given in the table below:

| $Q^1$ | -O—CO— | -O—$CH_2$— | -$CH_2$— | -$CH_2CH_2$— | -$CH_2$— | -$CH_2CH_2$— |
| --- | --- | --- | --- | --- | --- | --- |
| $Q^2$ | — | — | -CO—O— | -CO—O— | -$CH_2$—O— | -$CH_2$—O— |

In the preferred compounds of the formulae above and below, the alkyl radicals, in which, in addition, one $CH_2$ group (alkoxy or oxaalkyl) may be replaced by an O atom, may be straight-chain or branched. They preferably have 5, 6, 7, 8, 9 or 10 C atoms and accordingly are preferably pentyl, hexyl, heptyl, octyl, nonyl, decyl, pentoxy, hexoxy, heptoxy, octoxy, nonoxy or decoxy, furthermore also ethyl, propyl, butyl, undecyl, dodecyl, propoxy, ethoxy, butoxy, undecoxy, dodecoxy, 2-oxapropyl (=2-methoxymethyl), 2- (=ethoxymethyl) or 3-oxabutyl (=2methoxypentyl), 2-, 3- or 4-oxapentyl, 2-, 3-, 4- or 5-oxahexyl, or 2-, 3-, 4-, 5- or 6-oxaheptyl.

$A^1$ and $A^2$ are preferably Cy or Ph. In the compounds of the formulae above and below, Ph is preferably a 1,4-phenylene (Phe), a pyrimidine-2,5-diyl (Pyr), a pyridine-2,5-diyl (Pyn), a pyrazine-3,6-diyl or a pyridazine-2,5-diyl group, particularly preferably Phe, Pyr or Pyn. The compounds according to the invention preferably contain not more than one 1,4-phenylene group in which one or two CH groups are replaced by N. Cy is preferably a 1,4-cyclohexylene group. However, particularly preferred compounds of the formula I are those in which one of the groups $A^2$, $A^3$ and $A^4$ is a 1,4-cyclohexylene group which is substituted in the 1- or 4-position by CN and in which the nitrile group is in the axial position, i.e. the group $A^2$, $A^3$ or $A^4$ has the following configuration:

Particularly preferred compounds of the formula I and of the sub-formulae above are those which contain a -Ph-Ph-group. -Ph-Ph- is preferably -Phe-Phe-, Phe-Pyr or Phe-Pyn. Particularly preferred groups are

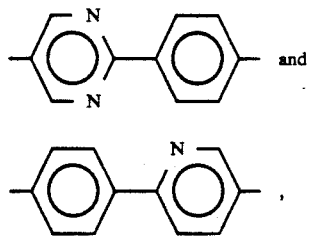

and furthermore 4,4'-biphenylyl which is unsubstituted or monosubstituted or polysubstituted by fluorine.

$Z^1$ and $Z^2$ are preferably single bonds, and secondarily preferably —O—CO—, —CO—O—, —C≡C— or —CH$_2$CH$_2$— groups.

$Z^1$ is particularly preferably —CO—O, —O—CO—, —C≡C— or —CH$_2$CH$_2$—, in particular the —CH$_2$CH$_2$— and the —C≡C— group.

In the compounds of the formulae above and below, X is halogen, CN or CH$_3$, preferably F, Cl, CH, or CN. F and CN are particularly preferred.

$R^o$ is an alkyl group which is different from X, is preferably straight-chain and preferably has up to 4 C atoms. Methyl and ethyl, in particular methyl, are particularly preferred.

The preferred meaning of $Q^1$ and $Q^2$ is alkylene having 1 or 2 C atoms, —O—, —O—CO—, —CO—O— and a single bond. Further preferred meanings of $Q^1$ and $Q^2$ are —CH$_2$O— and —O—CH$_2$—.

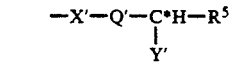

in which

X' is —CO—O—, —O—CO—, —O—CO—O—, —CO—, —O—, —S—, —CH=CH—, —CH=CH—COO— or a single bond, Q' is alkylene having 1 to 5 C atoms in which, in addition, one CH$_2$ group which is not linked to X' may be replaced by —O—, —CO—, —O—CO—, —CO—O— or —CH=CH—, or is a single bond, Y' is CN, halogen, methyl or methoxy, and $R^5$ is an alkyl group having 1 to 15 C atoms which is different from Y and in which, in addition, one or two non-adjacent CH$_2$ groups may be replaced by —O—, —CO—, —O—CO—, —CO—O— and/or —CH=CH—.

X' is preferably —CO—O—, —O—CO—, —O—, —CH=CH—COO— (trans) or a single bond. —O— or a single bond are particularly preferred.

Q' is preferably —CH$_2$—, —CH$_2$CH$_2$—, —CH$_2$CH$_2$CH$_2$— or a single bond, particularly preferably a single bond, —CH$_2$— or —CH$_2$CH$_2$—.

Y' is preferably CH$_3$, —CN, F or Cl, particularly preferably CN or F.

$R^5$ is preferably straight-chain or branched alkyl having 1 to 10, in particular 1 to 7, C atoms.

Of the compounds of the formula I', those are preferred in which X' and Y' are not simultaneously methyl.

The following 5 combinations of X', Q', Y' and R' are particularly preferred:

| X' | -O— | — | -O— or -CO—O— | -COO— or -O— | -OOC— |
|---|---|---|---|---|---|
| Q' | -CH$_2$— | -CH$_2$CH$_2$— | — | — | — |
| Y' | F | F | CH$_3$ | CN | F oder Cl |
| $R^5$ | -Alkyl | -Alkyl | -COO-Alkyl | Alkyl | Alkyl |

Compounds of the formulae above and below having branched wing groups $R^1$ may be important. Branched groups of this type generally contain not more than two chain branches. $R^1$ is preferably a straight-chain group or a branched group having not more than one chain branch.

Preferred branched radicals are isopropyl, 2-butyl (=1methylpropyl), isobutyl (=2-methylpropyl), tert.-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

The radical $R^1$ can also be an optically active organic radical having an asymmetric carbon atom. The asymmetric carbon atom in this case is preferably linked to two differently substituted C atoms, one H atom and one substituent selected from the group comprising halogen (in particular F, Cl or Br), alkyl or alkoxy, in each case having 1 to 5 C atoms, and CN. The optically active organic radical R' or Q* preferably has the formula Of the compounds of the formulae I and Ia to Ii, those are preferred in which at least one of the radicals present therein has one of the preferred meanings indicated.

In the compounds of the formula I and in the sub-formulae above and below, —(A$^1$—Z$^1$)$_m$—PheF$_2$—(Z$^2$—A$^2$)$_n$— is preferably a group of the following formulae 1 to 16 or the mirror image thereof;

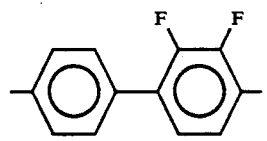

1

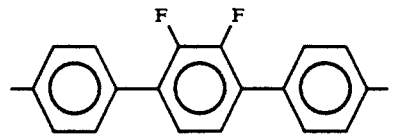

2

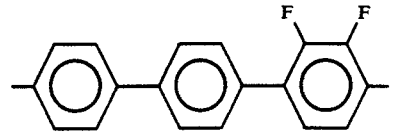

3

-continued

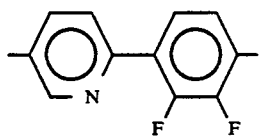
4

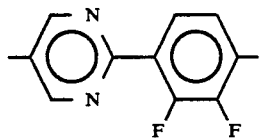
5

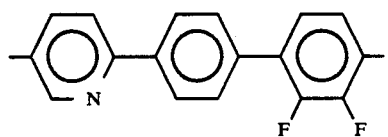
6

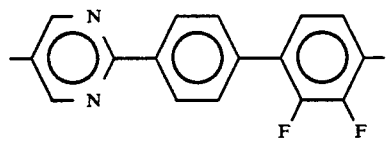
7

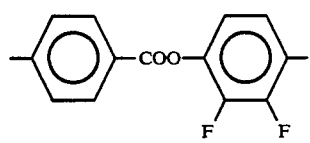
8

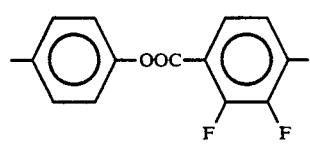
9

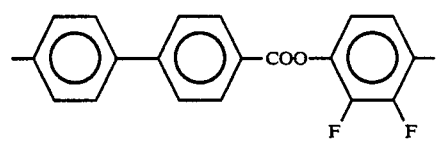
10

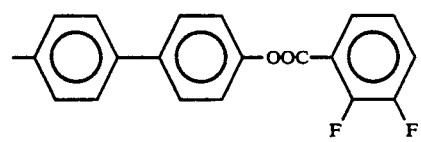
11

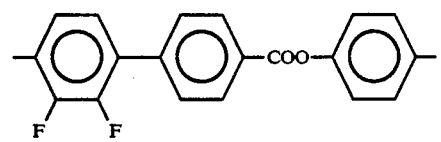
12

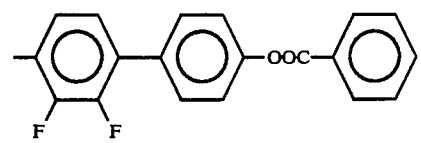
13

-continued

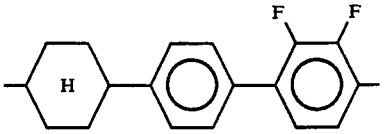
14

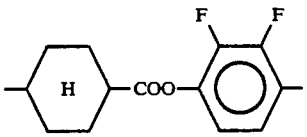
15

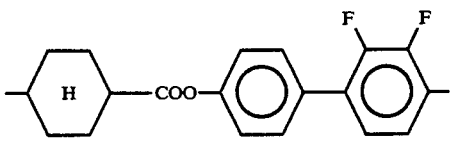
16

Groups of the formulae 1, 3, 4, 5, 7, 8, 10, 11, 12 and 13, in particular those of the formulae 1, 3, 4, 5 and 10–13 are particularly preferred.

Those of the abovementioned formulae which contain one or more groups Dio, Dit, Pip and/or Pyr in each case include the two possible 2,5-(Dio, Dit, Pyr) or 1,4-positional isomers (Pip).

A smaller group of particularly preferred dopes is that of the formulae:

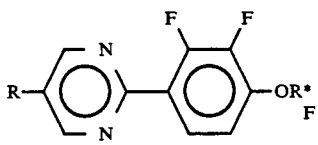
A

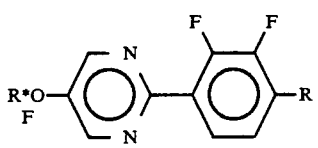
B

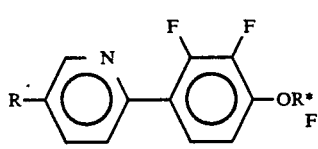
C

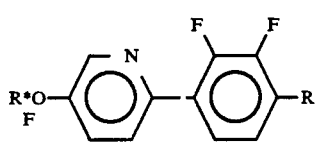
D

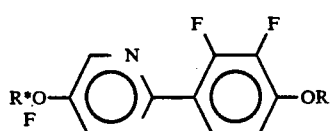
E

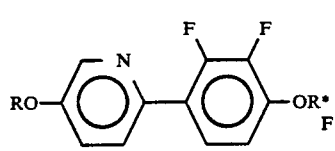
F

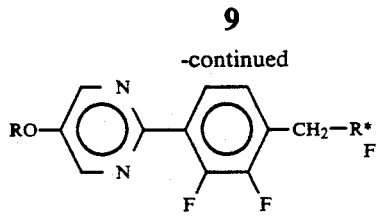

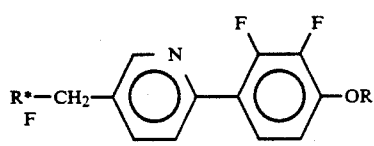

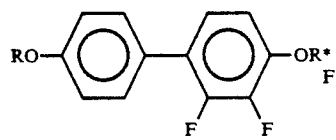

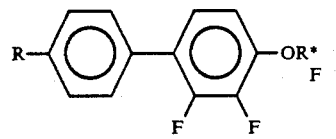

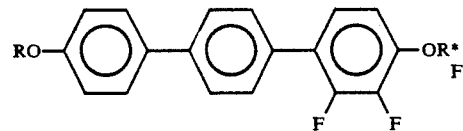

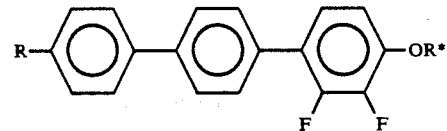

In these formulae, $R_F$ is straight-chain or monobranched (preferably a methyl branch) alkyl having 3 to 12 C atoms in which one $CH_2$ group has been replaced by —CHF— and C* is an asymmetric C atom. $R_F$ is preferably

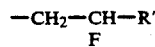

in which R' is straight-chain or monobranched (preferably a methyl branch) alkyl having 2 to 10, in particular 3 to 10, C atoms. R has one of the meanings for $R^1$ and is preferably alkyl, oxaalkyl or alkenyl preferably having 3 to 12, in particular 5 to 12, C atoms. R groups are preferably straight-chain. Particularly preferred compounds are furthermore those of above and below, the formula I in which —$(A^1—Z^1)_m$—$PheF_2$—$(Z^2—A^2)_n$— is

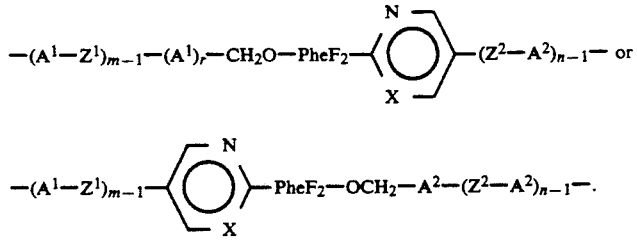

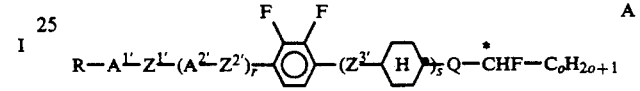

X is N or CH. r is 0 or 1.

In addition, particularly preferred compounds are the optically active compounds of the formula A R—$A^{1'}$—$Z^{1'}$—$(A^{2'}—Z^{2'})_r$—⟨F,F⟩—$(Z^{3'}$—⟨H⟩$)_s$—Q—*CHF—$C_oH_{2o+1}$  A in which R is an alkyl or alkenyl radical having up to 15 C atoms which is unsubstituted, monosubstituted by —CN or at least monosubstituted by fluorine or chlorine, it also being possible for one $CH_2$ group in these radicals to have been replaced by —O—, —CO—, —O—CO—, —CO—o— or —O—CO—O—, $A^{1'}$ and $A^{2'}$, in each case independently of one another, are a 1,4-phenylene radical which is unsubstituted or substituted by one or two fluorine atoms, or a pyridine-2,5-diyl radical, a pyrimidine-2,5-diyl radical, a pyrazine-2,5-diyl radical, a pyridazine-3,6-diyl radical, a 1,3,4-thiadiazole-2,5-diyl radical, a 1,2,4-thiadiazole-3,5-diyl radical, a trans-1,4-cyclohexylene radical in which, in addition, one or two nonadjacent $CH_2$ groups may be replaced by —O— and/or —S— and/or in which one CH group may be replaced by —C(CN)—, or a 1,4-cyclohexenylene radical, a 1,4-bicyclo(2.2.2)octylene radical or a piperidine-1,4-diyl radical, $Z^{1'}$, $Z^{2'}$ and $Z^{3'}$, in each case independently of one another, are —CO—O—, —O—CO—, —$CH_2O$—, —$CH_2CH_2$—, —CH=CH—, —C≡C— or a single bond, Q is —$OCH_2$—, —$COOCH_2$— or —$CH_2OCH_2$—, o is 1 to 12, and one of the two values r and s is 0 and the other is 0 or 1.

The compounds of the formula A can be prepared by methods known per se, for example by or analogously to the synthetic scheme below:

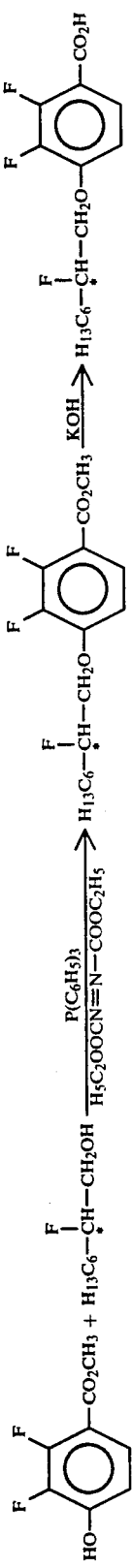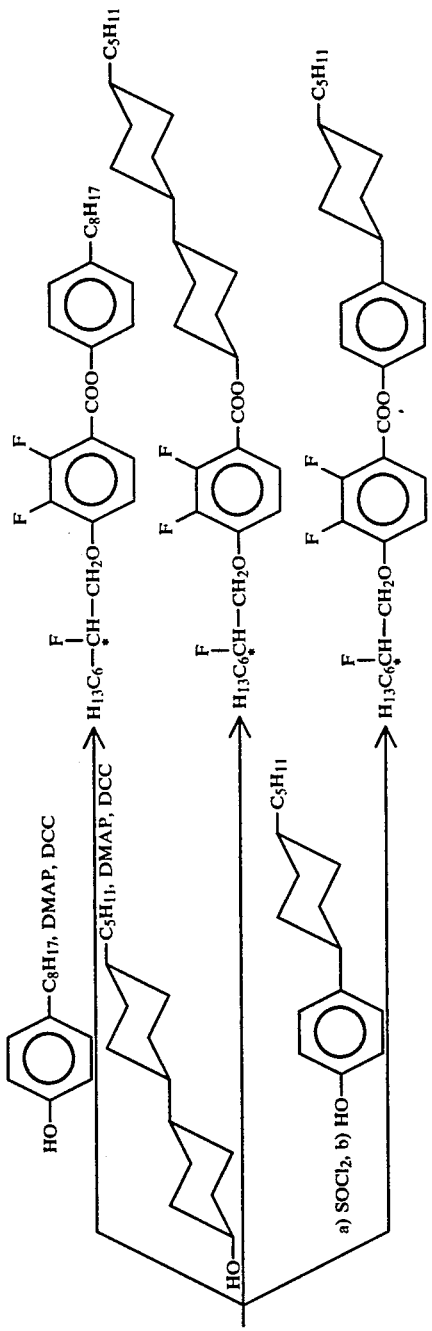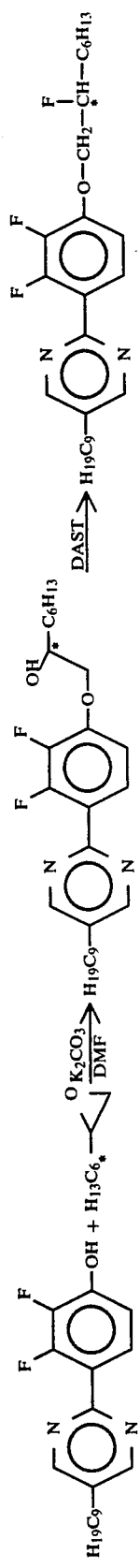

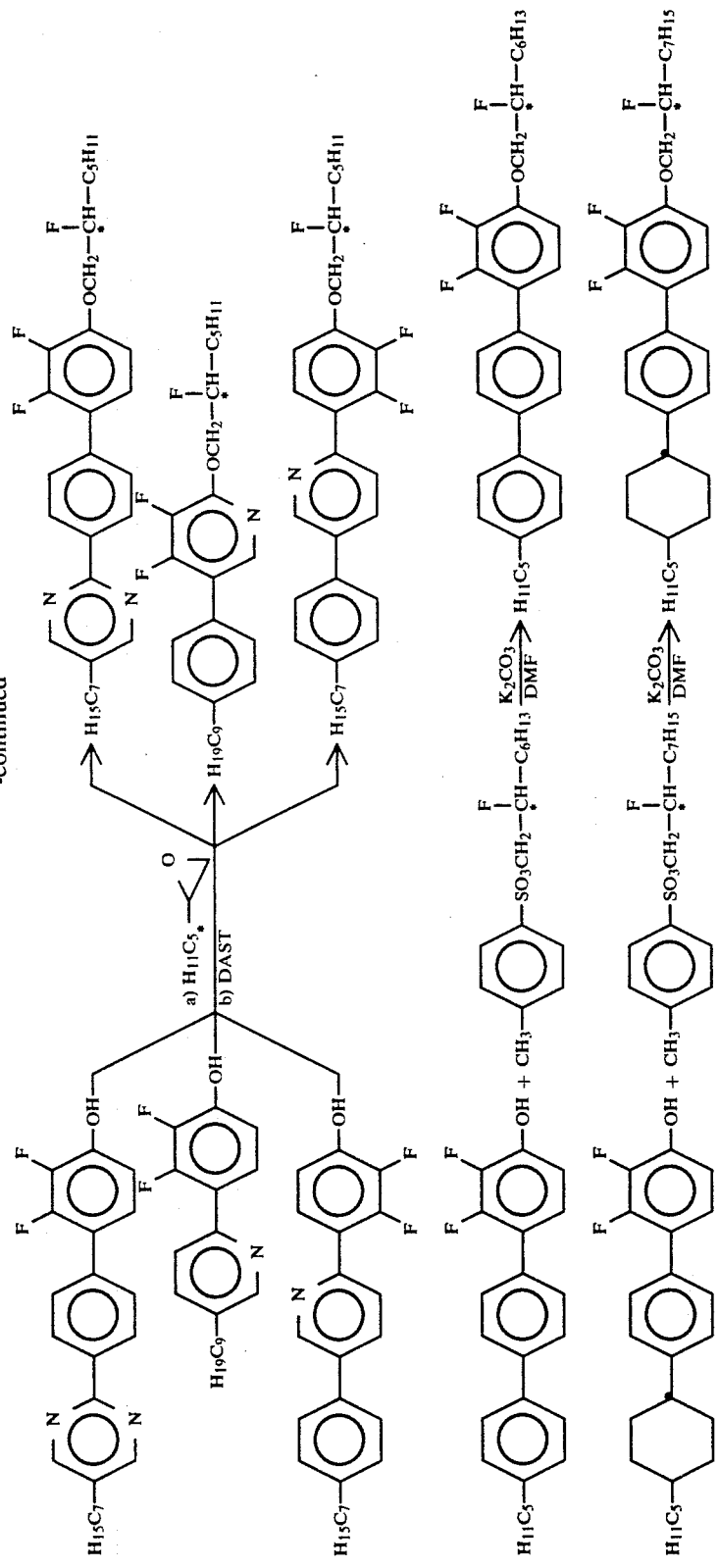

Particularly preferred compounds according to the invention are those of the sub-formula I2'

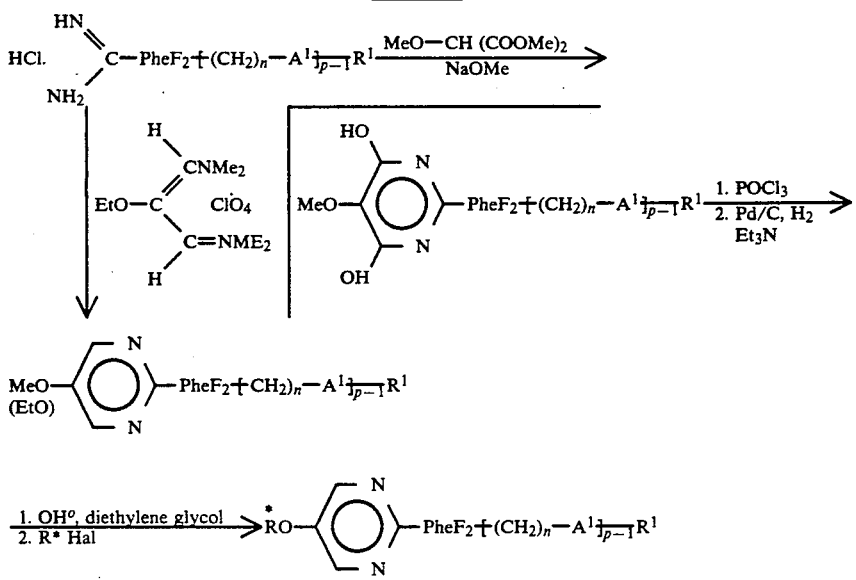

I2' p is 1 or 2. n, A¹, Q* and R¹ have the abovementioned meaning. A is a 1,3,4-thiadiazole-2,5-diyl, pyrimidine-2,5-diyl, pyridine-2,5-diyl or pyrazine-3,6-diyl group. A⁰ is preferably A particularly preferred smaller group of compounds is that of the formula I1'

I1' p is 1 or 2. n, Q*, A¹ and R¹ have the abovementioned meaning. The compounds of the formula I1' can be prepared as indicated in scheme 1 below:

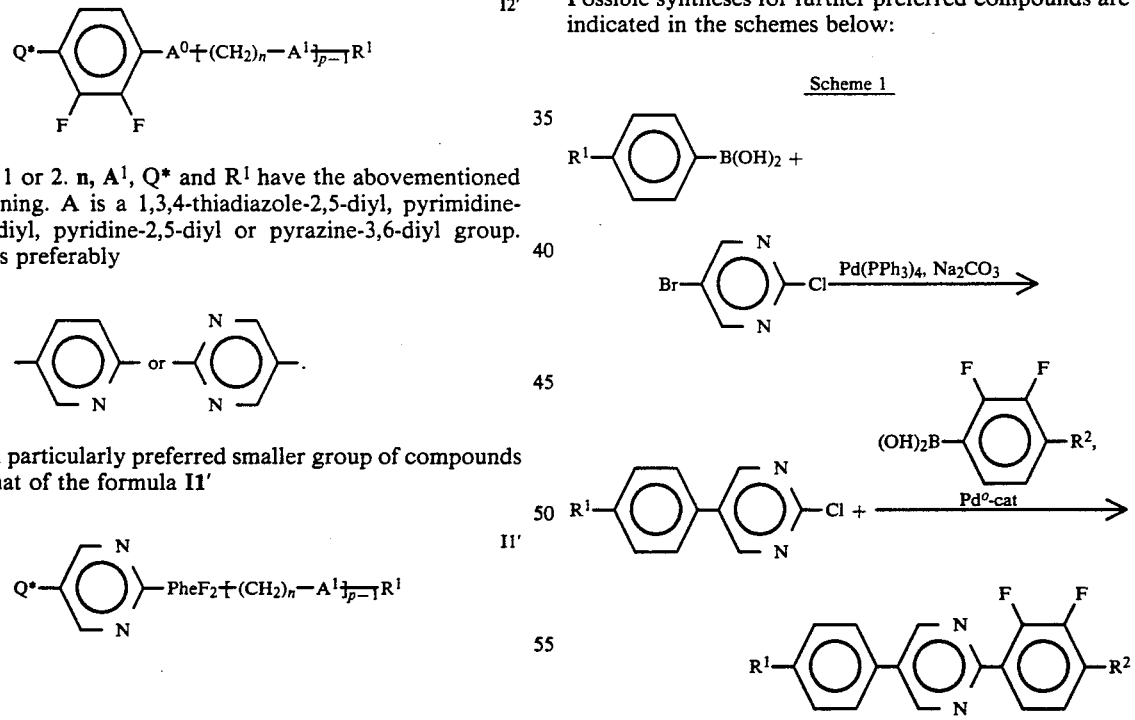

Possible syntheses for further preferred compounds are indicated in the schemes below:

Scheme 1

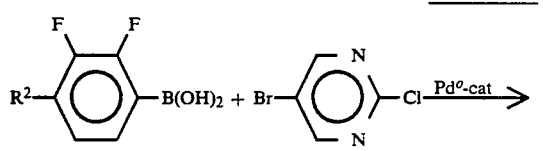

-continued
Scheme 3
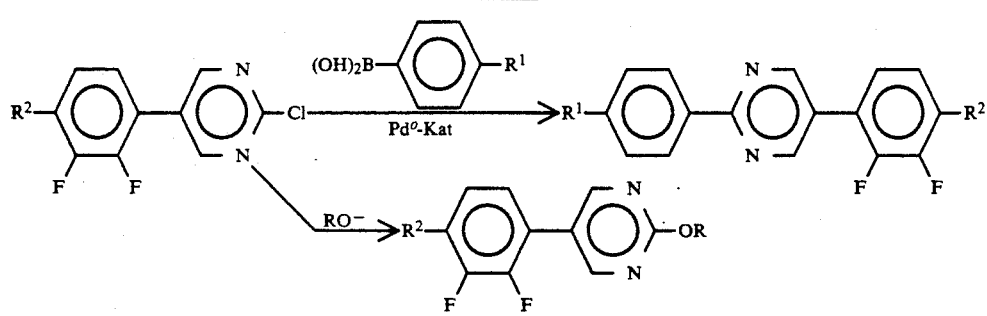
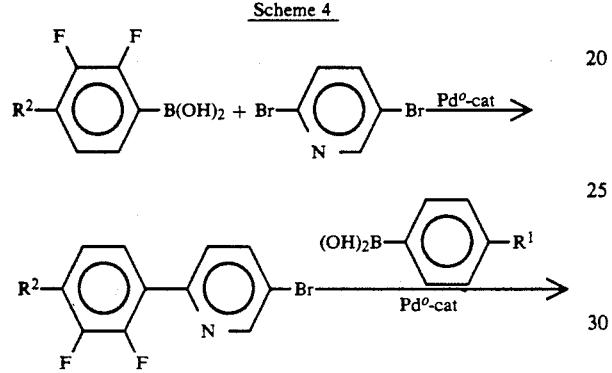
Scheme 4
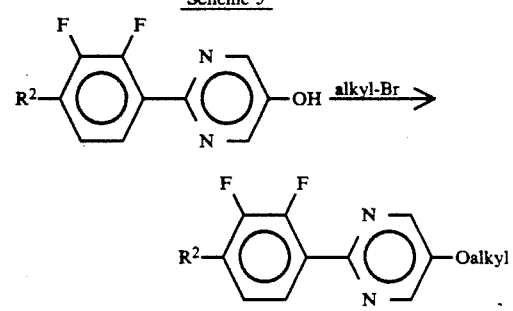
-continued
Scheme 5
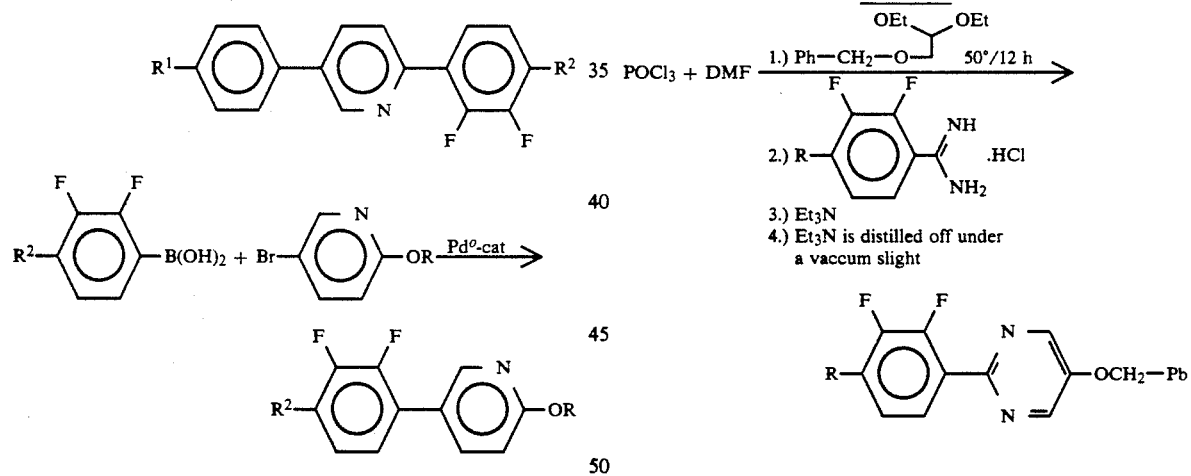
Scheme 5
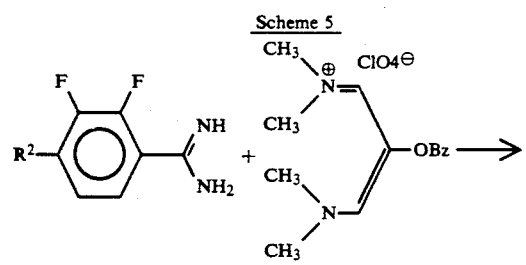
Scheme 6
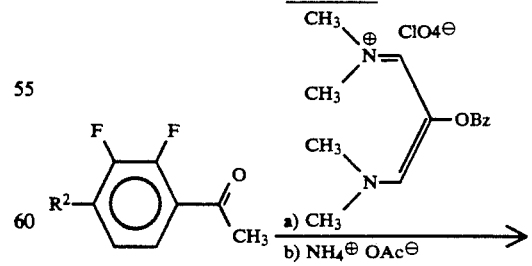
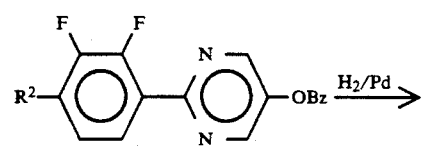

-continued
Scheme 6

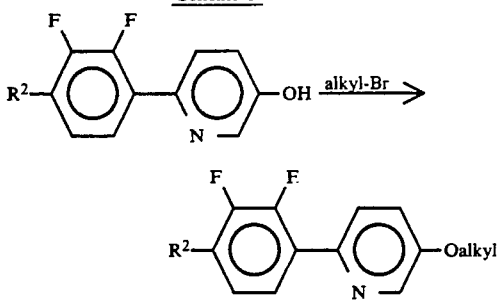

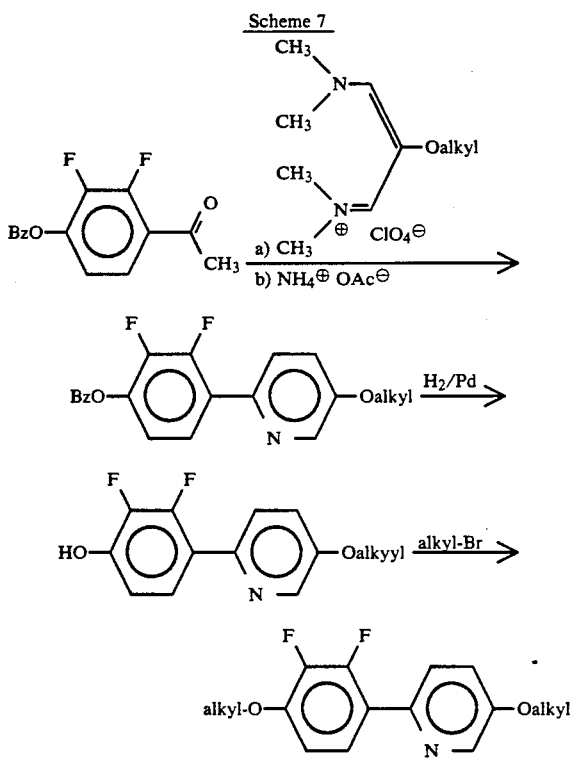

The compounds of the formula I are prepared by methods which are known per se, as described in the literature (for example in the standard works such as Houben-Weyl, Methoden der Organischen Chemie [Methods of organic chemistry], Georg-Thieme-Verlag, Stuttgart), to be precise under reaction conditions which are known and suitable for the reactions mentioned. Use can also be made here of variants which are known per se, but are not described in greater detail here.

If desired, the starting materials can also be formed in situ by not isolating them from the reaction mixture, but instead immediately reacting them further to form the compounds of the formula I.

Compounds of the formula I or precursors thereof are accessible starting from 1,2-difluorobenzene. The latter is metallated by known processes (for example A. M. Roe et al., J. Chem. Soc. Chem. Comm., 22, 582 (1965)) and reacted with the appropriate electrophile. This reaction sequence can be carried out a second time using a suitable electrophile with the 1-substituted 2,3-difluorobenzene obtained in this way, to give 1,4-disubstituted 2,3-difluorobenzenes (for example benzoic acids or phenols) which are suitable for the syntheses of the compounds of the formula I. 1,2-Difluorobenzene or 1-substituted 2,3-difluorobenzene is reacted with phenyllithium, lithium tetramethylpiperidine, or n-, sec- or tert-butyllithium at temperatures of from −100° C. to +50° C., preferably −78° C. to 0° C., in an inert solvent, such as diethyl ether, tetrahydrofuran, dimethoxyethane, tert-butyl methyl ether or dioxane, hydrocarbons, such as hexane, heptane, cyclohexane, benzene or toluene, or mixtures of these solvents, if appropriate with addition of a complexing agent, such as tetramethylethylenediamine (TMEDA) or hexamethylphosphoric triamide. Further details are given in German Offenlegungsschrift 3,807,910.

The lithium 2,3-difluorophenyl compounds are reacted with the appropriate electrophiles at −100° C. to 0° C., preferably at −50° C. Suitable electrophiles are aldehydes, ketones, nitriles, epoxides, carboxylic acid derivatives, such as esters, anhydrides or halides, haloformic acid esters or carbon dioxide.

For reaction with aliphatic or aromatic halogen compounds, the lithium 2,3-difluorophenyl compounds are transmetallated and coupled with transition-metal catalysis. Zinc 2,3-difluorophenyl compounds (cf. German Offenlegungsschrift 3,632,410) or titanium 2,3-difluorophenyl compounds (cf. German Offenlegungsschrift 3,736,489) are particularly suitable for this purpose.

The heterocyclic structural elements can be introduced on the one hand by converting precursors which already contain these structural elements into compounds of the formula I by known methods. On the other hand, however, a heterocyclic radical can be produced in appropriately structured precursors or substructure units of the compounds of the formula I by methods known per se. Thus, for example, 2,5-disubstituted 1,3,4-thiadiazoles can be prepared by reacting N,N'-diacylhydrazines with customary thiation reagents, such as $P_4S_{10}$ or Lawesson's reagent. The N,N'-diacylhydrazines are themselves accessible by known methods from the corresponding carboxylic acids, it being possible for the carboxylic acids having a 2,3-difluoro-1,4-phenylene structural element as described above to be obtained by reacting appropriate metallated precursors with carbon dioxide.

The 2,5-disubstituted pyrimidines can be prepared, for example, by reacting appropriate amidine hydrochlorides (which can be prepared from the corresponding carboxylic acids) with malondialdehyde tetramethyl acetals by methods known per se. The 2,5-disubstituted pyridines can be obtained by coupling organometallic zinc compounds with appropriate bromopyrimidine derivatives in accordance with German Offenlegungsschrift 3,632,410. The 2,5-disubstituted pyrazines can be obtained by condensation of suitably substituted ethylenediamines with glyoxal derivatives, oxidation of the dihydro compounds using atmospheric oxygen or other oxidants, and isolation of the 2,5-disubstituted pyrazines desired from the resultant mixture of 2,5- and 2,6-disubstitution products. The 3,6-disubstituted pyridazines are accessible by reacting 1,4-diketones (prepared, for example, by the method of Stetter by thiazolium salt-catalysed addition of an aldehyde to an α,β-unsaturated ketone) and subsequent oxidation of the dihydropyridazine using atmospheric oxygen or other oxidants such as potassium nitrite or chromic acid in glacial acetic acid.

The synthesis of some particularly important hydroxyl intermediates is described below:

a) 5-alkyl-2-(2,3-difluoro-4-hydroxyphenyl)pyridines can be obtained by reacting 2,3-difluoro-4-benzyloxybenzamidine hydrochloride with 2-alkyl-3-ethoxyacroleins or with 2-alkylated malonaldehyde tetraacetals or appropriately substituted vinylogous formamidinium salts (R. M. Wagner and CH. Jutz, Chem. Ber. 104 2975 (1971), by preferably heating the components in DMF (dimethylformamide) and subsequently removing the protecting group hydrogenolytically.

b) 5-Hydroxy-2-(2,3-difluoro-4-alkylphenyl)pyrimidines and 5-hydroxy-2(2,3-difluoro-4-alkoxyphenyl)pyrimidines [sic] can be obtained by condensation of 4-alkyl- or 4-alkoxy-2,4-difluorobenzamidine hydrochloride respectively with 2-benzyloxytrimethinium perchlorate (A. Holy, Z. Arnold; Collection Czechoslov. Chem. Comm. 38 1371–1380 (1973), or 2-benzyloxy-3-dimethylaminoacrolein (H. Horstmann et al., Arzneimittelforsch. 11 682 (1961) and subsequent hydrogenolysis of the benzyl group.

The corresponding 5-benzyloxypyrimidine is obtained by a one-pot process by adding an amidinium salt to a reaction mixture, which has been stirred for 12 hours at 50° C., of $POCl_3$, DMF and 2-benzyloxyacetaldehyde diethyl acetal and subsequently adding triethylamin an removing the triethylamine by distillation.

c) 5-Hydroxy-2(2,3-difluoro-4-alkylphenyl)pyridines [sic] and 5-hydroxy-2(2,3-difluoro-4-alkoxyphenyl)pyridines [sic] can be obtained from 2-benzyloxytrimethinium salt by condensation with 4-alkyl- or 4-alkoxy-2,3-difluoroacetophenones, reaction with $NH_3/NH_4Cl$ or ammonium acetate.

[sic] Analogously to the procedures of Ch. Jutz et al. (Liebigs Ann. Chem. 1975 874–900) and subsequent hydrogenolysis, or from 4-alkyl- or 4-alkoxy-2,3-difluorophenylboric acid by coupling with 5-acetoxy-2-bromopyridine (obtainable from 5-hydroxy-2-bromopyridine by esterification) in the presence of a Pd catalyst in accordance with the work of Suzuki et al. (Synth. Commun. 11 513–19 (1981)).

d) 5-Alkoxy-2(2,3-difluoro-4-hydroxyphenyl)pyridines [sic] can be obtained by coupling 2,3-difluoro-4-benzyloxyphenylboric acid with 5-alkoxy-2-bromopyridine in accordance with the abovementioned literature and subsequent hydrogenolysis.

e) 5-Alkyl-2(2,3-difluoro-4-hydroxyphenyl)pyridines [sic] can be obtained by coupling 2-bromo-5-methylpyridine with 2,3-difluoro-4-benzyloxyphenylboric acid and a Pd catalyst under the abovementioned conditions, extending the chain of the methyl group by deprotonation using LDA as base (−65° C.) and alkylation using an alkyl bromide and hydrogenolysis.

f) 4-Alkoxy-2',3'-difluoro-4'-hydroxybiphenyls and 4-alkyl-2',3'-difluoro-4'-hydroxybiphenyls can be obtained as described above starting from 1,2-difluorobenzene (cf. German Offenlegungsschrift 3,807,910).

g) 5-Alkyl-2(2,3-difluoro-4-hydroxyphenyl)pyrimidines [sic] and 5-alkoxy-2(2,3-difluoro-4-hydroxyphenyl)pyrimidines [sic] can be prepared by customary condensation of 2,3-difluoro-4-benzyloxybenzamidine with 2-alkylmalonaldehyde tetraacetals or 2-alkyl-3-ethoxyacroleins or 2,3-dialkoxyacroleins or the corresponding immonium salts or alkoxytrimethinium salts, and subsequent hydrogenolysis.

The particularly preferred compounds containing chiral fluoroalkyloxy or fluoroalkyl groups as Q* can be prepared as follows:

Commercially available optically active 1,2-epoxides are opened by the method of S. Brandange et al. (Acta Scand. B 37 (1983) 141–145) using HF/pyridine to form the corresponding optically active 2-fluoro-1-alkanols. The latter can be converted under standard conditions into the corresponding tosylates and then further into the iodides by the method of Finkelstein. The tosylates and the iodides are suitable as alkylating agents, tosylates preferably being employed for etherification of phenols. A further way of introducing optically active monofluorinated side chains is direct ring opening of optically active 1,2-epoxides by means of phenolates or suitable carbon nucleophiles. These ring openings proceed regiospecifically on the less-substituted C atom of the epoxide and give the corresponding optically active alcohols, which can then be converted under standard conditions using DAST into the optically active fluorine compounds. Carbon nucleophiles which are suitable for ring opening are, for example, Grignard compounds, acetylides, enolates, or alternatively methyl groups with an azide CH of heterocyclic compounds (for example pyridine) or suitable substituted aromatics (for example p-tolunitrile).

Thus, the compounds of the formula I can be prepared by reducing a compound which contains one or more reducible groups and/or C—C bonds in place of H atoms, but otherwise corresponds to the formula I.

Suitable reducible groups are preferably —CH═CH— groups, furthermore, for example, free or esterified hydroxyl groups, aromatically bound halogen atoms or carbonyl groups. Preferred starting materials for the reduction correspond to the formula I, but contain a —CH═CH— group in place of a —$CH_2CH_2$— group and/or contain a —CO— group in place of a —$CH_2$— group and/or contain a free or functionally derived (for example in the form of its p-toluenesulfonate) OH group in place of an H atom.

The reduction can be carried out, for example, by catalytic hydrogenation at temperatures between about 0° and about 200° and at pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid, or a hydrocarbon such as cyclohexane. Suitable catalysts are expediently noble metals such as Pt or Pd, which can be employed in the form of oxides (for example $PtO_2$ or PdO), on a support (for example Pd on charcoal, calcium carbonate or strontium carbonate), or in finely divided form.

Ketones can also be reduced by the methods of Clemmensen (using zinc, zinc amalgam or tin and hydrochloric acid, expediently in aqueous-alcoholic solution or in heterogeneous phase with water/toluene at temperatures between about 80° and 120°) to form the corresponding compounds of the formula I which contain alkyl groups and/or —$CH_2CH_2$— bridges.

In addition, reductions using complex hydrides are possible. For example, arylsulfonyloxy groups can be removed reductively using LiAlH , in particular p- toluenesulfonyloxymethyl groups can be reduced to methyl groups, expediently in an inert solvent such as diethyl ether or THF, at temperatures between about 0° and 100°. Double bonds can be hydrogenated (even in the presence of CN groups!) using $NaBH_4$ or tributyltin hydride in methanol; for example the corresponding cyclohexane derivatives are thus produced from 1-cyanocyclohexene derivatives.

Esters of the formula I can also be obtained by esterification of corresponding carboxylic acids (or reactive derivatives thereof) using alcohols or phenols (or reactive derivatives thereof).

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1-4 C atoms in the alkyl group.

Suitable reactive derivatives of the alcohols and phenols mentioned are, in particular, the corresponding metal alcoholates or phenolates, preferably of an alkali metal such as Na or K.

The esterification is advantageously carried out in the presence of an inert solvent. Highly suitable solvents are, in particular, ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as carbon tetrachloride or tetrachloroethylene, and sulfoxides, such as dimethyl sulfoxide or sulfolane. Water-immiscible solvents can at the same time advantageously be used for removal by azeotropic distillation of the water formed during the esterification. It may in some cases also be possible to use an excess of an organic base, for example pyridine, quinoline or triethylamine, as the solvent for the esterification. The esterification can also be carried out in the absence of a solvent, for example by simply heating the components in the presence of sodium acetate. The reaction temperature is usually between $-50°$ and $+250°$, preferably between $-20°$ and $+80°$. At these temperatures, the esterification reactions are generally complete after 15 minutes to 48 hours.

In detail, the reaction conditions for the esterification depend substantially on the nature of the starting materials used. Thus, the reaction of a free carboxylic acid with a free alcohol or phenol is generally carried out in the presence of a strong acid, for example a mineral acid such as hydrochloric acid or sulfuric acid. A preferred reaction procedure is to react an acid anhydride or, in particular, an acyl chloride with an alcohol, preferably in a basic medium, important bases being, in particular, alkali metal hydroxides, such as sodium hydroxide or potassium hydroxide, alkali metal carbonates or hydrogen carbonates, such as sodium carbonate, potassium carbonate or potassium hydrogen carbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification is to first convert the alcohol or the phenol, for example by treatment with ethanolic sodium hydroxide solution or potassium hydroxide solution, into the sodium alcoholate or phenolate or potassium alcoholate or phenolate, to isolate and suspend the latter with stirring in acetone or diethyl ether together with sodium hydrogen carbonate or potassium carbonate, and to add a solution of the acyl chloride or anhydride in diethyl ether, acetone or DMF to this suspension, expediently at temperatures between about $-25°$ and $+20°$. Dioxane derivatives and dithiane derivatives of the formula I are expediently prepared by reacting an appropriate aldehyde (or a reactive derivative thereof) with an appropriate 1,3-diol or an appropriate 1,3-dithiol (or a reactive derivative thereof), preferably in the presence of an inert solvent, such as benzene or toluene, and/or in the presence of a catalyst, for example a strong acid such as sulfuric acid, benzenesulfonic acid or p-toluenesulfonic acid, at temperatures between 20° and about 150°, preferably between 80° and 120°. Suitable reactive derivatives of the starting materials are primarily acetals.

Some of the aldehydes, 1,3-diols and 1,3-dithiols mentioned, and some of the reactive derivatives thereof, are known, but they can all be prepared without difficulties from compounds known from the literature by standard methods of organic chemistry. For example, the aldehydes can be obtained by oxidation of corresponding alcohols or by reduction of corresponding carboxylic acids or derivatives thereof, the diols can be obtained by reduction of corresponding diesters, and the dithiols can be obtained by reaction of corresponding dihalides with NaSH.

Ethers of the formula I can be obtained by etherification of corresponding hydroxyl compounds, preferably corresponding phenols, the hydroxyl compound expediently first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This metal derivative can then be reacted with the appropriate alkyl halide, sulfonate or dialkyl sulfate, expediently in an inert solvent, such as acetone, 1,2-dimethoxyethane, DMF or dimethyl sulfoxide, or alternatively an excess of aqueous or aqueous-alcoholic NaOH or KOH, at temperatures between about 20° and 100°.

In order to prepare the nitriles of the formula I or to prepare suitable precursors, it is also possible to react appropriate chlorine or bromine compounds of the formula I or suitable precursors with a cyanide, expediently with a metal cyanide, such as NaCN, KCN or $Cu_2(CN)_2$, for example in the presence of pyridine in an inert solvent, such as DMF or N-methylpyrrolidone, at temperatures between 20° and 200°.

The optically active compounds of the formula I are obtained by using corresponding optically active starting materials and/or by resolving the optical antipodes by means of chromatography by known methods.

The phases according to the invention preferably contain at least one, preferably at least two, compounds of the formula I. Particularly preferred chiral tilted smectic liquid-crystalline phases according to the invention are those whose achiral base mixture contains at least one other component having a negative dielectric anisotropy or a small positive dielectric anisotropy. The chirality is preferably based in part or in full on the chiral compounds of the formula I. These phases preferably contain one or two chiral compounds of the formula I. However, it is also possible for achiral compounds of the formula I (for example in the form of a racemate) to be employed, in which case the chirality of the phase is caused by other optically active compounds. If chiral compounds of the formula I are used, mixtures containing an enantiomeric excess are also suitable in addition to the pure optical antipodes. The other component(s) mentioned above for the achiral base mixture can make up 1 to 95%, preferably 10 to 90%, of the mixture. Suitable further components having a small positive or negative dielectric anisotropy are compounds of the sub-formulae IIa to IIg:

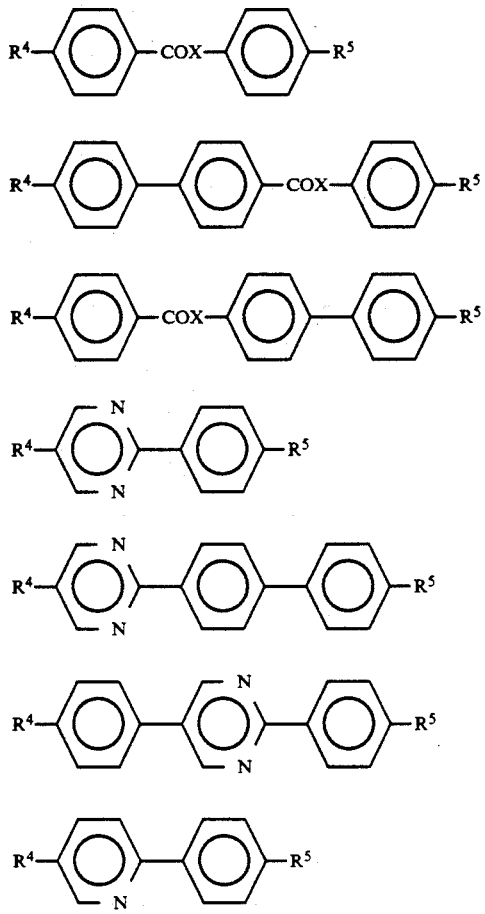

$R^4$ and $R^5$ are both preferably alkyl, alkoxy, alkanoyloxy or alkoxycarbonyl, in each case having 3 to 12 C atoms. X is preferably O. In the compounds of the formulae IIa to IIg, it is also possible for one 1,4-phenylene group to be laterally substituted by halogen, particularly preferably by fluorine. One of the groups $R^4$ and $R^5$ is preferably alkyl and the other group is alkoxy.

Particularly preferred compounds are those of the subformulae IIa to IIg in which $R^4$ and $R^5$ are each straight-chain alkyl or alkoxy, in each case having 5 to 10 C atoms.

Furthermore preferred phases according to the invention are those which, besides components of the formulae IIa to IIg, also contain at least one component having a clearly negative dielectric anisotropy ($\Delta\epsilon \leq -2$). Particularly suitable here are compounds of the formulae IIIa to IIIc

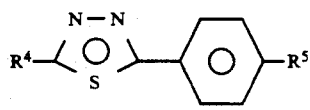

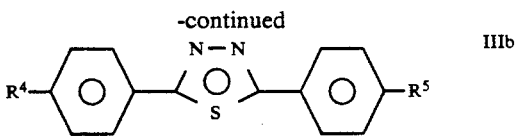

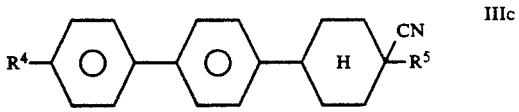

in which $R^4$ and $R^5$ have the general and preferred meanings given in the case of the formulae IIa to IIg. In the compounds of the formulae IIIa, IIIb and IIIc, it is also possible for one 1,4-phenylene group to be laterally substituted by halogen, preferably fluorine. The compounds of the formula I include, in particular, dinuclear and trinuclear materials. Of the dinuclear, which are preferred, those are preferred in which $R^1$ is n-alkyl or n-alkoxy having 7 to 12, in particular 7 to 9, C atoms.

The phases according to the invention preferably contain at least one trinuclear compound of the formula I. These phases are distinguished by particularly high $S_C/S_A$ transition temperatures.

The compounds of the formula I are also suitable as components of nematic liquid-crystalline phases, for example for avoiding reverse twist.

These liquid-crystalline phases according to the invention comprise 2 to 25, preferably 3 to 15 components, including at least one compound of the formula I. The other components are preferably selected from nematic or nematogenic substances, in particular known substances from the classes comprising the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4,-bis-cyclohexylbiphenyls, phenyl- or cyclohexylpyrimidines, phenyl- or cyclohexylpyridazines and the N-oxides thereof, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolans and substituted cinnamic acids.

The most important compounds which are suitable as components of liquid-crystalline phases of this type can be characterized by the formula I′

$$R'—L—G—E—R''  \qquad I''$$

in which L and E are each a carbocyclic or heterocyclic ring system from the group comprising 1,4-disubstituted benzene and cyclohexane rings, 4,4,-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline,

| G is | -CH=CH- | -N(O)=N- |
|---|---|---|
| | -CH=CY- | -CH=N(O)- |
| | -C≡C- | -CH₂-CH₂- |
| | -CO-O- | -CH₂-O- |
| | -CO-S- | -CH₂-S- |
| | -CH=N- | -COO-Phe-COO- |
| | or a C—C single bond, | |
| | Y is halogen, preferably chlorine, or -CN, and | |

R' and R'''are alkyl, alkoxy, alkanoyloxy, alkoxycarbonyl or alkoxycarbonyloxy having up to 18, preferably up to 8, carbon atoms, or one of these radicals is alternatively CN, NC, NO$_2$, CF$_3$, F, Cl or Br.

In most of these compounds, R' and R'' are different from one another, one of these radicals usually being an alkyl or alkoxy group. However, other variants of the proposed substituents are also common. Many such substances or mixtures thereof are commercially available. All these substances can be obtained by methods which are known from the literature.

The phases according to the invention contain about 0.1 to 99, preferably 10 to 95%, of one or more compounds of the formula I. Additionally preferred liquid-crystalline phases according to the invention are those which contain 0.1–40, preferably 0.5–30%, of one or more compounds of the formula I.

The phases according to the invention are prepared in a manner which is customary per se. In general, the components are dissolved in one another, expediently at elevated temperature.

By means of suitable additives, the liquid-crystalline phases according to the invention can be modified in a manner such that they can be used in all types of liquid-crystal display elements which have been disclosed hitherto.

Additives of this type are known to those skilled in the art and are described in detail in the literature. For example, conductive salts, preferably ethyldimethyldodecylammoniun 4-hexyloxybenzoate, tetrabutylammonium tetraphenylborate or complex salts of crown ethers (cf., for example, I. Haller et al., Mol. Cryst. Liq. Cryst. Volume 24, pages 249–258 (1973)) can be added in order to improve the conductivity, pleochroic dyes can be added to produce coloured guest-host systems or substances can be added to modify the dielectric anisotropy, the viscosity and/or the orientation of the nematic phases.

Substances of this type are described, for example, in German Offenlegungsschrift 2,209,127, 2,240,864, 2,321,632, 2,338,281, 2,450,088, 2,637,430, 2,853,728 and 2,902,177.

The examples below are intended to illustrate the invention without representing a limitation. Mp.=melting point, Cp.=clear point. Above and below, percentages are percent by weight; all temperatures are given in degrees Celsius. "Customary work-up" means that water is added, the mixture is extracted with methylene chloride, the organic phase is separated off, dried and evaporated, and the product is purified by crystallization and/or chromatography.

In addition, the abbreviations have the following meanings:

C: crystalline solid state, S: smectic phase (the index denotes the phase type), N: nematic state, Ch: cholesteric phase, I: isotropic phase. The number between two symbols indicates the transition temperature in degrees Celsius.

EXAMPLE 1 a) 323 g of butyraldehyde and 422 g of ethyl cyanoacetate are dissolved in 750 ml of glacial acetic acid, 15 g of piperidine are added, and the reaction mixture is stirred, during which it warms to about 55° C. After the reaction mixture has been cooled to room temperature, 20 g of 5% Pd-C catalyst are added, and the mixture is then hydrogenated at 30° and an H$_2$ pressure of 2 bar until the calculated amount of hydrogen has been taken up (about 7 hours). After the catalyst has been separated off, the hydrogenation solution is evaporated on a rotary evaporator, the residue is taken up in..methyl tertiary-butyl ether (MTB ether), and the solution is washed by shaking twice with water and subsequently with 5% NaHCO$_3$ solution. The organic phase is dried and evaporated. The residue is distilled in vacuo ($2\times 10^{-2}$ mbar) (62° C. to 78°), to give ethyl 2-butylcyanoacetate.

b) With exclusion of oxygen and atmospheric moisture, 450 ml of diisopropylamine, 539 g of ethyl 2-butylcyanoacetate dissolved in 400 ml of THF, and then 200 ml of methyl iodide, likewise dissolved in 200 ml of THF, are added successively at −60° C. to 2000 ml of a 1.6N solution of butyllithium (BuLi) in hexane and 2000 ml of tetrahydrofuran (THF). The mixture is allowed to warm slowly to room temperature, and is stirred for 12 hours and worked up in the customary manner. 256 g of KOH pellets (85%) are dissolved in 3000 ml of methanol. 595 g of ethyl 2-butyl-2-methylcyanoacetate are then added with ice cooling, and the mixture is stirred for 3 hours with further ice cooling. The reaction mixture is then acidified using concentrated HCl, diluted with water and extracted with MTB ether. The ether phase is extracted with 10% NaHCO$_3$ solution, and the extract is re-acidified using concentrated HCl with ice cooling. The product is re-extracted from the aqueous phase using MTB ether, and the organic phase is washed several times with saturated sodium chloride solution, then dried and evaporated.

c) Racemate resolution 455 g of 2-butyl-2-methylcyanoacetic acid and 908 g of quinine are dissolved in 2000 ml of THF with gentle warming, and the solution is stirred for 2 hours. The solution is cooled to room temperature and then added slowly with vigorous stirring to 6000 ml of hexane cooled to −50° C. The mixture is stirred at −40°/−50° C. for 4 hours, and the precipitate is then filtered off with suction and dried in vacuo. The salt is recrystallized several times from hexane/THF until the melting point of 146.7° C. has been reached, and the acid is then liberated in the customary manner.

$\alpha^{20}_D$ (CHCl$_3$): +6.3 d) To [sic] 129 g of 2-butyl-2-methylcyanoacetic acid are warmed to 60° C. together with a catalytic amount of dimethylformamide (DMF) and 120 ml of SOCl$_2$ are then slowly added dropwise. Vigorous evolution of gas sets in. When this has subsided, the mixture is refluxed for 2 hours, excess SOCl$_2$ is removed by distillation in vacuo, and the residue is fractionated ($4\times 10^{-2}$ mbar, 52°–53° C.).

e) 0.1 mol of 4'-heptyloxy-2,3-difluoro-4-hydroxybiphenyl (preparation: 0.1 mol of 2,3-difluoro-4'-heptyloxybiphenyl (prepared by metallation of 2,3-difluorobenzene using BuLi in the presence of tetramethylethylenediamine (TMEDA) in THF at −80° C. and reaction with heptyloxycyclohexanone [sic] and subsequent dehydration using toluene/toluenesulfonic acid on a water separator and aromatization using DDQ) are dissolved in 200 ml of THF and 0.1 mol of TMEDA, the mixture is cooled to −78° C., metallated at this temperature in 0.105 mol of a 1.6N solution of BuLi in hexane and stirred for 3 hours. In the interim, 70 ml of a 2N solution of ethylmagnesium bromide in ether are added over the course of 30 minutes to a solution of 0.12 mol of tert.-butyl hydroperoxide in 50 ml of ether. The solution prepared in this way is carefully added dropwise to the solution, cooled to −78° C., of the metallated 2,3-difluoro-4-heptyloxybiphenyl, and the mixture is then allowed to warm to room temperature and then stirred for a further 2 hours. After customary workup, 4-hydroxy-2,3-difluoro-4'-heptyloxybiphenyl is obtained) and 0.11 mol of pyridine are introduced into toluene, and a solution of 2-methyl-2-butylcyanoacetyl chloride in a little toluene is added at 50°–60° C. The mixture is then stirred at the temperature indicated for 5 hours and worked up in a customary manner, to give optically active 4'-heptyloxy-2,3-difluorobiphenyl-4-yl 2-butyl-2-methylcyanoacetate.

EXAMPLE 2

At 0° C., 0.1 mol of DCC, dissolved in methylene chloride, is added to a mixture of 0.1 mol of 4'-heptyloxy-2,3-difluorobiphenylcarboxylic acid (preparation: 0.1 mol of 2,3-difluoro-4'-heptyloxybiphenyl and 0.1 mol of TMEDA are dissolved in 200 ml of THF, and the solution is cooled to −78° C. and reacted at this temperature with 0.105 mol of a 1.6N solution of BuLi in hexane. The reaction mixture is stirred at −78° C. for 3 hours and then tipped in one portion onto 200 g of powdered dry ice. After customary work-up, 4'-heptyloxy-2,3-difluorobiphenyl-4-carboxylic acid is obtained), 0.1 mol of optically active 2-cyano-2-methylhexan-1-ol (which can be prepared from optically active ethyl 2-methyl-2-butylcyanoacetate by reduction using $LiBH_4$) and a catalytic amount of 4-N,N'-dimethylaminopyridine (DMAP) in 200 ml of methylene chloride. The mixture is subsequently stirred at room temperature for 12 hours and worked up in a customary manner, and the product is purified by crystallization, to give optically active 2-cyano-2-methylhexyl 4'-heptyloxy-2,3-difluorobiphenyl-4-carboxylate.

EXAMPLE 3

0.17 mol of diethyl azodicarboxylate (DEAD), dissolved in THF, is added to a solution of 0.15 mol of 4'-heptyloxy-2,3-difluorobiphenyl-4-ol, 0.17 mol of L(−)-ethyl lactate and 0.15 mol of triphenylphosphine in 400 ml of THF. During this operation, a reaction temperature of 50° C. must not be exceeded. The mixture is stirred for 1 hour at 50° C. and then overnight at room temperature. The solvent is then removed by distillation, the residue is dissolved in hot toluene, and the solution is then left to cool slowly. The triphenylphosphine oxide which precipitates is filtered off with suction, the filtrate is evaporated and the residue is purified by chromatography, to give ethyl 2-[4-(p-heptyloxyphenyl)-2,3-difluorophenoxy]propionate.

The following compound is prepared analogously:
ethyl 2-[4-(5-nonylpyrimidin-2-yl)-2,3-difluorophenoxy]-propionate.

EXAMPLE 4

At 0° C., a solution of 0.05 mol of dicyclohexylcarbodiimide (DCC) in methylene chloride is added to 0.05 mol of 4'-heptyloxy-2,3-difluorobiphenyl-4-carboxylic acid, 0.05 mol of L(−)-ethyl lactate and a catalytic amount of DMAP in 70 ml of methylene chloride. The mixture is subsequently stirred at room temperature for 12 hours, the urea which has precipitated is then filtered off with suction, and the mixture is worked up in the customary manner, to give optically active ethyl 2-[4-(p-heptyloxyphenyl)-2,3-difluorobenzoyloxy]propionate.

EXAMPLE 5

Optically active benzyl lactate is esterified by means of DCC and a catalytic amount of DMAP with 4,-heptyloxy-2,3-difluorobiphenyl-4-carboxylic acid, and the benzyl group is subsequently removed hydrogenolytically. 0.01 mol of the acid obtained in this way is converted into the corresponding acyl chloride in 50 ml of benzene at room temperature in the presence of catalytic amounts of DMF with 0.02 mol of oxalyl chloride. The reaction mixture is evaporated in vacuo and the residue is taken up in 30 ml of diglyme. 25 ml of a 30% aqueous ammonia solution are added dropwise with cooling and vigorous stirring. The mixture is stirred at room temperature for 2 hours and diluted with water, and the precipitate is filtered off with suction, washed thoroughly with water and dried in vacuo. 40 ml of DMF and 0.08 mol of thionyl chloride are subsequently added to the precipitate. When the gas evolution has subsided, the mixture is stirred at room temperature for a further 2 hours, then carefully hydrolysed and worked up in a customary manner. The product is purified by chromatography, to give optically active 1-cyanoethyl 4'-heptyloxy-2,3-difluorobiphenyl-4-carboxylate.

EXAMPLE 6

Optically active benzyl lactate is etherified by means of diethyl azodicarboxylate (DEAD)/triphenylphosphine with 4'-heptyloxy-2,3-difluorobiphenyl-4-ol, and the benzyl group is subsequently removed hydrogenolytically. The acid obtained in this way is converted into the nitrile in the customary manner (oxalyl chloride, ammonia and thionyl chloride), to give optically active 4'-heptyloxy-2,3-difluoro-4-(1-cyanoethlyxy)biphenyl [sic].

EXAMPLE 7

At 0° C., a solution of 0.1 mol of DCC in methylene chloride is added to a mixture of 0.1 mol of 4,-heptyloxy-2,3-difluorobiphenyl-4-ol, 0.1 mol of optically active 2-chloro-3-methylbutyric acid (prepared from valine) and a catalytic amount of DMAP in 250 ml of methylene chloride. The mixture is subsequently stirred at room temperature for 12 hours, the precipitate is then filtered off with suction, and the filtrate is worked up in a customary manner, to give 4-(p-heptyloxyphenyl)-2,3-difluorophenyl 2-chloro-3-methylbutyrate.

The following are prepared analogously by esterification of analogous chiral α-halocarboxylic acids using 5-alkyl-2-(2,3-difluoro-4-hydroxyphenyl) pyrimidines:
4-(5-heptylpyrimidin-2-yl)-2,3-difluorophenyl 2-fluorooctanoate, m.p. 39°
4-(5-heptylpyrimidin-2-yl)-2,3-difluorophenyl 2-chloro-3-methylbutyrate, m.p. 65°

EXAMPLE 8

At 0° C., 0.1 mol of DCC, dissolved in methylene chloride, is added with exclusion of moisture to a mixture of 0.1 mol of pentanoic acid, 0.1 mol of optically active 4'-heptyloxy-2,3-difluoro-4(2-hydroxypropyl) biphenyl [sic] (which can be prepared by customary metallation of 4'-heptyloxy-2,3-difluorobiphenyl and reaction with optically active propylene oxide) and a catalytic amount of DMAP in 200 ml of methylene chloride. When the addition is complete, the mixture is stirred at room temperature for 12 hours, the precipitate is filtered off with suction, and the product is worked up in a customary manner. The product is purified by chromatography, to give optically active 4'-heptyloxy-2,3-difluoro-4-(2-valeroyloxypropyl)biphenyl.

EXAMPLE 9

At 0° C., 0.1 mol of DCC, dissolved in methylene chloride, is added with exclusion of moisture to a mixture of 0.1 mol of pentanoic acid, 0.1 mol of optically active 2-(4'-heptyloxy-2,3-difluorobiphenyl-4-oxy)propan-1-ol (prepared by reduction of the corresponding ethyl lactate using LiBH$_4$) and a catalytic amount of DMAP in 250 ml of methylene chloride. The mixture is subsequently stirred at room temperature for 12 hours, the precipitate is filtered off with suction, and the filtrate is worked up in a customary manner, to give optically active 4'-heptyloxy-2,3-difluoro-4-(1-valeroyloxy-2-propyloxy)biphenyl.

EXAMPLE 10

Optically active benzyl S-2-hydroxy-3-methylbutyrate (prepared from the caesium salt of L-α-hydroxyisovaleric acid by reaction with benzyl bromide in DMF) and 4'-heptyloxy-2',3'-difluorobiphenyl-4-carboxylic acid (prepared by metallation of heptyloxy-2,3-difluorobenzene using BuLi and TMEDA in THF at −70° C., transmetallation using chlorotriisopropyl orthotitanate and subsequent reaction with ethyl 4-cyclohexanonecarboxylate, dehydration, aromatization using DDQ and hydrolysis using ethanolic KOH at 5° C.) is esterified by means of DCC and a catalytic amount of DMAP, and the benzyl group is subsequently removed hydrogenolytically. 0.01 mol of the acid obtained in this way is converted into the acyl chloride using 0.02 mol of oxalyl chloride in 75 ml of toluene at 25° C. in the presence of a catalytic amount of DMF. The reaction mixture is evaporated in vacuo, the residue is taken up in a little diglyme, and 30 ml of a 30% aqueous ammonia solution are added dropwise with vigorous stirring. The mixture is stirred at room temperature for two [sic] 2 hours and diluted with water, and the precipitate is filtered off with suction, washed with water until free from ammonia, and dried in vacuo. 40 ml of DMF and, dropwise, 0.1 mol of thionyl chloride are subsequently added. The mixture is stirred at room temperature for 2 hours and poured onto ice/water. The product is worked up in a customary manner and purified by chromatography, to give 1-cyano-2-methylpropyl 4'-heptyloxy-2',3'-difluorobiphenyl-4-carboxylate.

The following are prepared analogously:
1-cyano-2-methylpropyl 4'-heptyloxy-2,2',3'-trifluorobiphenyl-4-carboxylate
1-cyano-2-methylpropyl 4'-heptyloxy-3,2',3'-trifluorobiphenyl-4-carboxylate
1-cyano-2-methylpropyl 4'-heptyloxy-2,3,3'-trifluorobiphenyl-4-carboxylate
1-cyano-2-methylpropyl 4'-heptyloxy-2,3,2'-trifluorobiphenyl-4-carboxylate

EXAMPLE 11

2,3-Difluorohydroquinone monobenzyl ether (prepared from 2,3-difluorophenol by the Elbs reaction, benzylation of the sulfate obtained as an intermediate, and acid cleavage of the sulfate) is reacted with DEAD/PPh$_3$ and optically active ethyl lactate. The protecting group is subsequently removed hydrogenolytically. At 0° C., 0.01 mol of the compound obtained in this way and 0.01 mol of 4'-heptyloxybiphenyl-4-carboxylic acid are reacted dropwise with 0.01 mol of DCC dissolved in methylene chloride, with exclusion of moisture in methylene chloride in the presence of a catalytic amount of DMAP [sic]. The mixture is stirred at room temperature for 12 hours, the dicyclohexylurea which precipitates is removed by filtration, and the filtrate is worked up in a customary manner. The product is purified by chromatography, to give ethyl 2-[2,3-difluoro-4-(p-(p-heptyloxyphenyl)benzoyloxy)phenoxy]propionate.

EXAMPLE 12

0.08 mol of 5-heptyl-2-(2,3-difluoro-4-hydroxyphenyl)pyrimidine, together with 11.6 g of K$_2$CO$_3$ and 25.6 g of optically active 2-fluoro-1-octyl tosylate in 70 ml of methyl ethyl ketone, are refluxed for 12 hours under a protective gas atmosphere. The reaction mixture is then hydolysed [sic], and the product is then worked up in a customary manner and purified by chromatography, to give optically active 5-n-heptyl-2-[2,3-difluoro-4-(2-fluorooctyloxy)phenyl]pyrimidine of melting point 56° C.

All other suitable phenols and hydroxyl compounds can also be reacted with chiral 2-fluoro-1-alkyl tosylates in an entirely analogous manner.

EXAMPLE 13

0.04 mol of 5-(3-hydroxynonyl)-2-(2,3-difluoro-4-octyl-oxyphenyl)pyridine (optically active) [which can be prepared from 5-methyl-2-(2,3-difluoro-4-octyloxyphenyl)pyridine by reaction with LDA at −70° C. and addition of optically active 1,2-epoxyoctane] is dissolved in CH$_2$Cl$_2$ at −30° C. with exclusion of moisture. 8 ml of DAST, dissolved in 15 ml of CH$_2$Cl$_2$, are slowly added dropwise to this solution with cooling. The reaction mixture is then stirred at room temperature for 12 hours and subsequently hydrolysed using ice water. The product is worked up in a customary manner, to give optically active 5-(3-fluorononyl)-2-(2,3-difluoro-4-octyloxyphenyl)pyridine.

EXAMPLE 14

0.08 mol of 2,3-difluoro-4-(3-fluorononyl)benzamidine hydrochloride (optically active) [which can be obtained from 2,3-difluoro-4-methylbenzonitrile by reaction with LDA at −70° C. and addition of chiral 1,2-epoxyoctane, reaction of the alcohol produced with DAST, and conversion of the nitrile group into the amidine] is heated for 24 hours in DMF together with 0.1 mol of 2-heptyl-3-ethoxyacrolein. Customary work-up gives optically active 5-n-heptyl-2-[2,3-difluoro-4-(3-fluoro-n-nonyl)phenyl]-pyrimidine.

The corresponding 5-n-alkoxypyrimidines are obtained from 2,3-dialkoxyacroleins in an analogous manner.

EXAMPLE 15

0.05 mol of methyl 2,3-difluoro-4-hydroxybenzoate, 0.05 mol of (S)-2-fluorooctan-1-ol and 0.06 mol of triphenylphosphine are dissolved in 125 ml of tetrahydrofuran, and 0.06 mol of diethyl azodicarboxylate is added dropwise with stirring and ice cooling. The mixture is allowed to warm to room temperature and is stirred for a further 8 hours. The solvent is then removed by distillation, and the methyl 2,3-difluoro-4-(2-fluorooctyloxy)benzoate is purified by column chromatography. 2,3-Difluoro-4-(2-fluorooctyloxy)benzoic acid is obtained therefrom by hydrolysis using aqueous/alcoholic potassium hydroxide solution.

0.01 mol of this acid, 0.001 mol of 4-dimethylaminopyridine and 0.01 mol of 4-n-octylphenol are introduced into 15 ml of dichloromethane, a solution of 0.01 mol of dicyclohexylcarbodiimide is added dropwise at 10° with stirring, and the mixture is subsequently stirred at room temperature for a further 15 hours. The mixture is filtered through silica gel, and the solvent is evaporated to give, as residue, (S)-(4-n-octylphenyl)-2,3-difluoro-4-(2-fluorooctyloxy) benzoate.

EXAMPLE 16

Analogously to Example 15, (S)-[trans,trans-4-(4-n-pentylcyclohexyl)cyclohexyl] 2,3-difluoro-4-(2-fluorooctyloxy)benzoate is obtained when trans,trans-4-(4-pentylcyclohexyl)cyclohexanol is employed as the alcohol component in the esterification described above.

EXAMPLE 17

0.01 mol of (S)-2,3-difluoro-4-(2-fluorooctyloxy)-benzoyl chloride (prepared from the acid described in Example 15 by heating with thionyl chloride), 0.01 mol of 4-trans-4-n-pentylcyclohexyl)phenol and 0.01 mol of pyridine are refluxed for 2 hours in 20 ml of toluene. After cooling, the pyridine hydrochloride is filtered off with suction, the toluene is evaporated, and the (S)-[4-(trans-4-n-pentylcyclohexyl)phenyl] 2,3-difluoro-4-(2-fluorooctyloxy)benzoate remaining is recrystallized from ethanol.

EXAMPLE 18

0.05 mol of 2-(2,3-difluoro-4-hydroxyphenyl)-5-n-nonylpyrimidine, 0.5 mol of potassium carbonate and 40 ml of dimethylformamide are refluxed with stirring. 0.05 mol of (R)-1,2-epoxyoctane are added dropwise in the course of 5 minutes, and the mixture is left to react for a further 16 hours. The reaction mixture is subsequently poured onto 100 g of ice, and the (R)-2-[2,3-difluoro-4-(2-hydroxyoctyloxy)phenyl]-5-n-nonylpyrimidine which precipitates is filtered off with suction, washed with water and recrystallized from acetone.

0.03 mol of this compound is dissolved in 40 ml of dichloromethane and added dropwise at −70° under nitrogen to a stirred solution of 0.045 mol of diethylaminosulfur trifluoride in 15 ml of dichloromethane. The mixture is allowed to warm slowly to room temperature and left to react overnight. Water is then added to the reaction mixture with cooling, the mixture is stirred for 30 minutes, and the organic phase is separated off, washed with water and dried. After the solvent has been removed by distillation, (S)-2-[2,3-difluoro-4-(2-fluorooctyloxy)phenyl]-5-n-nonylpyrimidine is recrystallized from ethanol.

EXAMPLES 19-21

Analogously to Example 18, the compounds
(S)-2,3-difluoro-4-(2-fluoroheptyloxy)-4'-(5-n-heptylpyrimidin-2-yl)biphenyl,
(S)-2-[2,3-difluoro-4-(2-fluoroheptyloxy)phenyl]-5-n-nonylpyridine and
(S)-2-[2,3-difluoro-4-(2-fluoroheptyloxy)phenyl]-5-(4-n-heptylphenyl)pyridine
are obtained from the corresponding phenols by reaction with (R)-1,2-epoxyheptane and subsequent fluorination using diethylaminosulfur trifluoride.

EXAMPLE 22

0.02 mol of 2,3-difluoro-4-hydroxy-4'-pentyl-p-terphenyl, 0.02 mol of potassium carbonate and 0.2 mol of (S)-2-fluorooctyl p-toluenesulfonate (prepared from (S)-2-fluorooctan-1-ol and toluenesulfonyl chloride in the presence of pyridine) are stirred at 60° for 15 hours in 25 ml of dimethylformamide. The undissolved salts are filtered off with suction, and water is added to the filtrate. Extractive work-up and subsequent column chromatography give the pure (S)-2,3-difluoro-4-(2-fluorooctyloxy)-4'-pentyl-p-terphenyl.

EXAMPLE 23

Analogously to Example 22, (S)-2,3-difluoro-4-(2-fluorononyloxy)-4'-(trans-4-pentylcyclohexyl)biphenyl is obtained from 2,3-difluoro-4-hydroxy-4'-(trans-4-petnylcyclohexyl)biphenyl [sic] by etherification using (S)-2-fluorononyl-p-toluenesulfonate.

The examples below relate to liquid-crystalline phases according to the invention:

Example [sic] A to L

An achiral $S_C$ base mixture comprising
4.4% of 2-p-heptyloxyphenyl-5-heptylpyrimidine,
4.4% of 2-p-octyloxyphenyl-5-heptylpyrimidine,
4.4% of 2-p-nonyloxyphenyl-5-heptylpyrimidine,
7.8% of 2-(2,3-difluoro-4-octyloxyphenyl)-5-heptylyrimidine,
7.8% of 2-p-hexyloxyphenyl-5-nonylpyrimidine,
25.6% of 2-p-nonyloxyphenyl-5-nonylpyrimidine,
10.0% of 2-(2,3-difluoro-4-nonyloxyphenyl)-5-nonylpyrimidine,
8.9% of 2-(p-hexyloxyphenyl)-5-(p-heptylphenyl)-1,3,4-thiadiazole,
11.1% of r-1-cyano-cis-4-(4'-octyloxybiphenyl-4-yl)-1-octylcyclohexane,
8.9% of 2-(4'-hexyloxy-2,3-difluorobiphenyl-4-yl)-5-heptylpyrimidine and
6.7% of 2-(2,3-difluoro-4-pentyl-oxyphenyl)-5-(p-heptylphenyl)-1,3,4,-thiadiazole [sic]
is treated with 10% of each of the dopes A to L below. The phase transition temperatures and the values for the spontaneous polarization at room temperature are collated in the table below:

| Dope | $S_C^*$ | $S_A$ | Ch | I | $P_S$ (nC/cm$^2$) |
|---|---|---|---|---|---|
| A | 65 | 70 | 81 |  | 20 |
| B | 62 | — | 78 |  | 11 |
| C | 56 | 61 | 74 |  | 21 |
| D | 67 | 72 | 84 |  | 14 |
| E | 62 | 64 | 75 |  | 10 |
| F | 70 | 73 | 87 |  | 17 |
| G | 63 | 67 | 78 |  | 12 |
| H | 64 | — | 79 |  | 12 |
| I | 51 | 58 | 73 |  | 11 |
| J | 60 | 65 | 76 |  | 10 |
| K | 58 | 62 | 77 |  | 25 |

-continued

| Dope | $S_C^*$ | $S_A$ | Ch | I | $P_S$ (nC/cm²) |
|---|---|---|---|---|---|
| L | | 72 | 78 | 88 | 18 |

Dope types
A: 4'-Heptyloxy-2,3-difluorobiphenyl-4-yl 2-butyl-2-methylcyanoacetate
B: Ethyl 2-[4-(p-heptyloxyphenyl)-2,3-difluorophenoxy]-propionate
C: 1-Cyanoethyl 4'-heptyloxy-2,3-difluorobiphenyl-4-carboxylate
D: 4-(p-Heptyloxyphenyl)-2,3-difluorophenyl 2-chloro-3-methylbutyrate
E: 4'-Heptyloxy-2,3-difluoro-4-(1-valeroyloxy-2-propyloxy)biphenyl
F: Ethyl 2-[4-(4'-nonyloxy-2',3'-difluorobiphenyl-4-yl)phenoxy]propionate
G: 2-Cyano-2-methylhexyl 4'-heptyloxy-2,3-difluorobiphenyl-4-carboxylate
H: Ethyl 2-[4-(p-heptyloxyphenyl)-2,3-difluorobenzoyloxy]propionate
I: 4'-Heptyloxy-2,3-difluoro-4-(1-cyanoethoxy)biphenyl
J: 4'-Heptyloxy-2,3-difluoro-4-(2-valeroyloxypropyl)-biphenyl
K: 1-Cyano-2-methylpropyl 4'-heptyloxy-2',3'-difluorobiphenyl-4-carboxylate
L: Ethyl 2-[2,3-difluoro-4-(p-(p-heptyloxyphenyl)benzoyloxy)phenoxy]propionate [sic]

We claim:
1. A chiral 1,2-difluorobenzene compound of formula I

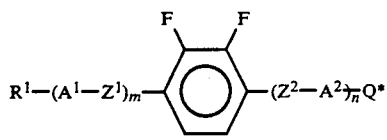

I in which
R¹ is an alkyl group having 1 to 12 C atoms and in which, in addition, one or two non-adjacent CH₂ groups may be replaced by O atoms and/or —CO— groups and/or —CO—O— groups and/or —CH=CH— groups and/or —CHhalogen— and/or —CHCN— groups,
Q* is a chirality-inducing organic radical having an asymmetric carbon atom, of the formula

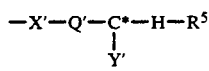

in which
X' is —CO—O—, —O—CO—, —O—CO—O—, —CO—O—, —S—, —CH=CH—, —CH=CH—, —CH=CH—COO— or a single bond,
O' is a single bond or alkylene having 1 to 5 C atoms in which, in addition, one CH₂ group which is not linked to X' may be replaced by —O—, —CO—, —O—CO—, —CO—O—, or —CH=CH—,
Y' is N, halogen, methyl or methoxy, and
R⁵ is an alkyl group having 1 to 15 C atoms which is different from X and in which, in addition, one or two non-adjacent CH₂ groups may be replaced by —O—, —CO—, —O—CO—, —CO—O—, or —CH=CH—,
or Q* is a chirality-inducing organic radical of the formula —Z¹—C*R⁰X—Q²—R²
in which
Q¹ and Q² in each case independently of one another, are a single handed, alkylene having 2 to 4 C atoms in which, in addition, one CH₂ may be replaced by —O—, —S—, —CO—, —O—CO—, —CO—O—, —S—CO— —CO—S—, —CH=CH—COO—, —CH=CH—, —CHhalogen— and/or —CHCN—,
X is halogen, CN, CH₃, CH₂CN or OCH₃,
R⁰ is an alkyl group having 1 to 10 C atoms which is different from X and —Q²—R², and C* is a carbon atom which is linked to four different substituents,
wherein

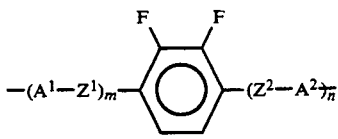

is selected from the group consisting of the formulae 1 to 8 or the mirror image thereof:

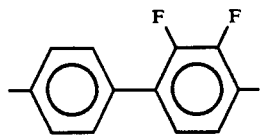

1

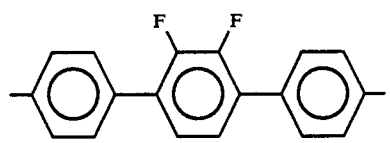

2

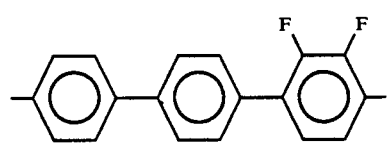

3

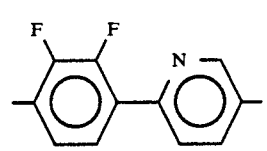

4

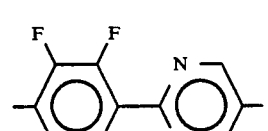

5

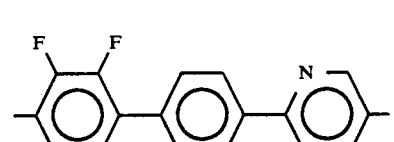

6

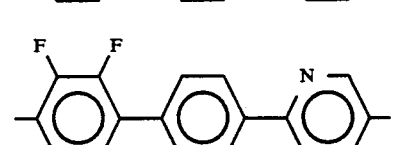

7

2. A compound according to claim 1, selected from the group consisting of formulae A to M:

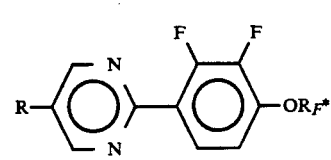

A

-continued

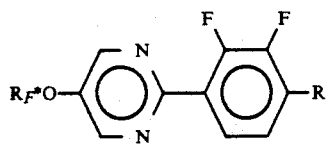

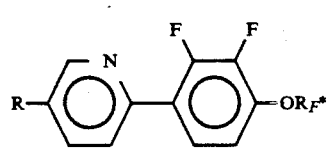

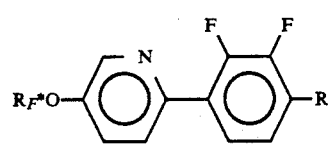

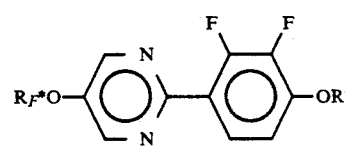

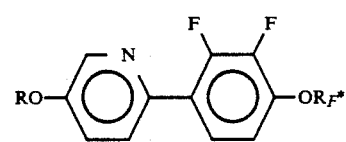

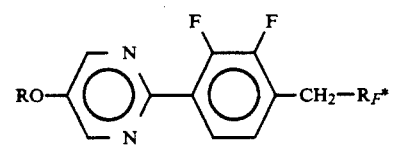

B

C

D

E

F

G

-continued

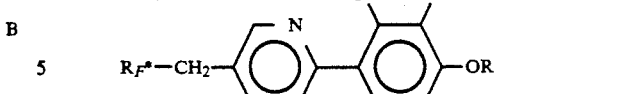 H

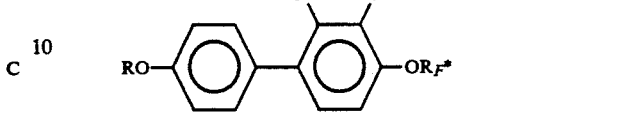 I

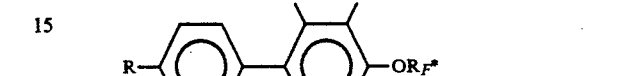 K

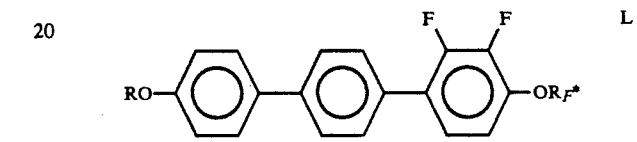 L and

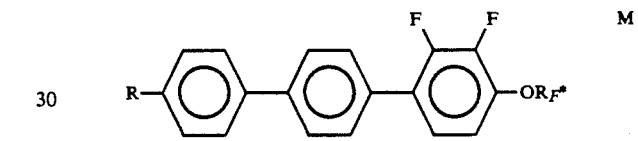 M in which
$R^F$ is straight-chain or mono-branched alkyl having 3 to 12 C atoms in which one $CH_2$ group has been replaced by —CHF— and R has one of the meanings given for $R^1$.

3. A chiral tilted smectic liquid-crystalline phase having at least two liquid-crystalline components, wherein at least one component is a compound of formula I according to claim 1.

4. A ferroelectric display element containing a dielectric, wherein the dielectric is a phase according to claim 3.

* * * * *